(12) United States Patent
Banas et al.

(10) Patent No.: US 6,214,039 B1
(45) Date of Patent: *Apr. 10, 2001

(54) COVERED ENDOLUMINAL STENT AND METHOD OF ASSEMBLY

(75) Inventors: Christopher E. Banas, Mesa; Rajagopal R. Kowligi; Roy H. Tang, both of Phoenix, all of AZ (US)

(73) Assignee: IMPRA, Inc., a subsidiary of C. R. Bard, Inc., Tempe, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,846
(22) PCT Filed: Aug. 24, 1995
(86) PCT No.: PCT/US95/10752
   § 371 Date: Feb. 18, 1998
   § 102(e) Date: Feb. 18, 1998
(87) PCT Pub. No.: WO97/07751
   PCT Pub. Date: Mar. 6, 1997
(51) Int. Cl.$^7$ .................................................. A61F 2/06
(52) U.S. Cl. .................. 623/1.13; 623/1.27; 623/1.32; 623/1.44
(58) Field of Search .................. 623/1, 12, 1.2, 623/1.13, 1.12, 1.32, 1.27, 1.18; 606/198

(56) References Cited

U.S. PATENT DOCUMENTS

| 4,300,244 | 11/1981 | Bokros . |
| 4,304,010 | 12/1981 | Mano . |
| 4,416,028 | 11/1983 | Eriksson et al. . |
| 4,503,569 | 3/1985 | Dotter . |
| 4,512,338 | 4/1985 | Balko . |

(List continued on next page.)

FOREIGN PATENT DOCUMENTS

| 3918736 | 12/1990 | (DE) . |
| 0221570 | 5/1987 | (EP) . |

(List continued on next page.)

OTHER PUBLICATIONS

Richard R. Heuser, et al Endoluminal Grafting for Percutaneous Aneurysm Exclusion in an Aortocoronary Saphenous Vein Graft: The First Clinical Experience, Journal of Endovascular Surgery. vol. 2, No. 1, Feb. 1995, pp. 81–129.

William A. Marston et al. Transbrachial Endovascular Exclusion of an Axillary Artery Pseudoaneurysm with PTFE–Covered Stents, Journal of Endovascular Surgery. vol. 2, No. 2, May 1995 pp. 172–176.

(List continued on next page.)

*Primary Examiner*—David H. Willse
*Assistant Examiner*—Suzette J. Jackson
(74) *Attorney, Agent, or Firm*—Morrison & Foerster LLP; Todd W. Wight (57) ABSTRACT

A radially expandable endoluminal covered stent assembly and a method and apparatus for making the same. A longitudinally and radially expanded polytetrafluoroethylene tubular graft is circumferentially engaged about one or more radially expandable stents and is retained thereon by a radial recoil force exerted by the tubular graft against the stent. The graft is retained on the stent or stents prior to and during endoluminal delivery and radial expansion without the use of adhesives, sutures or other attachment means. Further, upon radial expansion the stent or stents do not require retaining means for preventing contraction, despite the inherent recoil imparted by the tubular graft. The covered stent is assembled by joining a dilation mandrel and a stent mandrel, placing the graft on the dilation mandrel where it is radially expanded, and passing the expanded graft over the stent that is positioned on the stent mandrel.

15 Claims, 3 Drawing Sheets

U.S. PATENT DOCUMENTS

| | | |
|---|---|---|
| 4,546,500 | 10/1985 | Bell. |
| 4,562,596 | 1/1986 | Kornberg. |
| 4,580,568 | 4/1986 | Gianturco. |
| 4,604,762 | 8/1986 | Robinson. |
| 4,647,416 | 3/1987 | Seiler, Jr. et al.. |
| 4,718,907 | 1/1988 | Karwoski et al.. |
| 4,731,073 | 3/1988 | Robinson. |
| 4,733,665 | 3/1988 | Palmaz. |
| 4,739,762 | 4/1988 | Palmaz. |
| 4,743,480 | 5/1988 | Campbell et al.. |
| 4,749,585 | 6/1988 | Greco et al.. |
| 4,776,337 | 10/1988 | Palmaz. |
| 4,804,381 | 2/1989 | Turina et al.. |
| 4,816,339 | 3/1989 | Tu et al.. |
| 4,834,747 | 5/1989 | Gogolewski. |
| 4,850,999 | 7/1989 | Planck. |
| 4,892,544 | 1/1990 | Frisch. |
| 4,902,290 | 2/1990 | Fleckenstein et al.. |
| 4,922,905 | 5/1990 | Strecker. |
| 4,955,899 | 9/1990 | Della Corna et al.. |
| 4,969,896 | 11/1990 | Shors. |
| 4,986,831 | 1/1991 | King et al.. |
| 5,035,708 | 7/1991 | Alchas et al.. |
| 5,061,276 | 10/1991 | Tu et al.. |
| 5,078,726 | 1/1992 | Kreamer. |
| 5,084,065 | 1/1992 | Weldon et al.. |
| 5,102,417 | 4/1992 | Palmaz. |
| 5,104,399 | 4/1992 | Lazarus. |
| 5,104,400 | 4/1992 | Berguer et al.. |
| 5,122,154 | 6/1992 | Rhodes. |
| 5,123,917 | 6/1992 | Lee. |
| 5,152,782 | 10/1992 | Kowligi et al.. |
| 5,156,620 | 10/1992 | Pigott. |
| 5,163,951 | 11/1992 | Pinchuk et al.. |
| 5,181,903 | 1/1993 | Vann. |
| 5,192,310 | 3/1993 | Herweck et al.. |
| 5,192,311 | 3/1993 | King et al.. |
| 5,195,984 | 3/1993 | Schatz. |
| 5,201,778 | 4/1993 | Brotzu et al.. |
| 5,211,658 | 5/1993 | Clouse. |
| 5,217,483 | 6/1993 | Tower. |
| 5,219,355 | 6/1993 | Parodi et al.. |
| 5,236,447 | 8/1993 | Kubo et al.. |
| 5,246,452 | 9/1993 | Sinnott. |
| 5,282,846 | 2/1994 | Schmitt. |
| 5,282,848 | 2/1994 | Schmitt. |
| 5,282,860 | 2/1994 | Matsuno et al.. |
| 5,316,023 | 5/1994 | Palmaz et al.. |
| 5,330,500 | 7/1994 | Song. |
| 5,334,201 | 8/1994 | Cowan. |
| 5,354,329 | 10/1994 | Whalen. |
| 5,360,443 | 11/1994 | Barone et al.. |
| 5,382,261 | 1/1995 | Palmaz. |
| 5,383,926 | 1/1995 | Lock et al.. |
| 5,385,580 | 1/1995 | Schmitt. |
| 5,387,235 | 2/1995 | Chuter. |
| 5,389,106 | 2/1995 | Tower. |
| 5,405,377 | 4/1995 | Cragg. |
| 5,433,996 | 7/1995 | Kranzler et al.. |
| 5,443,496 | 8/1995 | Schwartz et al.. |
| 5,449,373 | 9/1995 | Pinchasik et al.. |
| 5,456,713 | 10/1995 | Chuter. |
| 5,489,295 | 2/1996 | Piplani et al.. |
| 5,496,364 | 3/1996 | Schmitt. |
| 5,507,771 | 4/1996 | Gianturco. |
| 5,522,883 | 6/1996 | Slater et al.. |
| 5,527,353 | 6/1996 | Schmitt. |
| 5,527,355 | 6/1996 | Ahn. |
| 5,540,712 | 7/1996 | Kleshinski et al.. |
| 5,540,713 | 7/1996 | Schnepp-Pesch et al.. |
| 5,549,663 | 8/1996 | Cottone, Jr.. |
| 5,556,414 | 9/1996 | Turi. |
| 5,571,170 | 11/1996 | Palmaz et al.. |
| 5,571,171 | 11/1996 | Barone et al.. |
| 5,571,173 | 11/1996 | Parodi. |
| 5,591,197 | 1/1997 | Orth et al.. |
| 5,591,223 | 1/1997 | Lock et al.. |
| 5,591,224 | 1/1997 | Schwartz et al.. |
| 5,591,228 | 1/1997 | Edoga. |
| 5,591,229 | 1/1997 | Parodi. |
| 5,628,786 | * 5/1997 | Banas et al. ............ 623/1 |
| 5,749,880 | 5/1998 | Banas et al.. |
| 5,769,884 | * 6/1998 | Solovay ............ 623/1 |
| 5,788,626 | * 8/1998 | Thompson ............ 623/1 |
| 5,800,522 | * 9/1998 | Cambell et al. ............ 623/1 |
| 5,824,043 | * 10/1998 | Cottone, Jr. ............ 623/1 |
| 5,824,046 | * 10/1998 | Smith et al. ............ 623/1 |
| 5,858,556 | * 1/1999 | Eckert et al. ............ 423/586 |
| 5,993,489 | * 11/1999 | Lewis et al. ............ 623/1.13 |
| 6,001,125 | * 12/1999 | Golds et al. ............ 623/1.13 |
| 6,004,348 | * 12/1999 | Banas et al. ............ 623/1.13 |
| 6,086,610 | * 7/2000 | Duerig et al. ............ 623/1.13 |
| 6,139,573 | * 10/2000 | Sogard et al. ............ 623/1.13 |

FOREIGN PATENT DOCUMENTS

| | | |
|---|---|---|
| 0335341 | 10/1989 | (EP). |
| 0461791 | 12/1991 | (EP). |
| 0551179 | 7/1993 | (EP). |
| 0646365 | 4/1995 | (EP). |
| 0662307 | 7/1995 | (EP). |
| 0667132 | 8/1995 | (EP). |
| 0656196 | 6/1996 | (EP). |
| 1505591 | 3/1978 | (GB). |
| WO 95/05132 | 2/1995 | (WO). |
| WO 95/05277 | 2/1995 | (WO). |
| WO 95/05555 | 2/1995 | (WO). |

OTHER PUBLICATIONS

Gerald Dorros, et al. Closure of a Popliteal Arteriovenous Fistula Using an Autologous Vein–Covered Palmas Stent, Journal of Endovascular Surgery. vol. 2, No. 2, May 1995 pp. 177–181.

Edward B. Diethrich et al. Endoluminal Grafting for Aneurysmal and Occlusive Disease in the Superficial Femoral Artery: Early Experience. Journal of Endovascular Surgery. vol. 2, No. 3, Aug. 1995 pp. 225–239.

* cited by examiner

COVERED ENDOLUMINAL STENT AND METHOD OF ASSEMBLY

BACKGROUND OF THE INVENTION

The present invention relates generally to a radially expandable endoluminal covered stent assembly and a method and apparatus for making the same. More particularly, the present invention relates to a longitudinally and radially expanded polytetrafluoroethylene (ePTFE) tubular graft which is circumferentially engaged about at least one balloon expandable endoluminal stent and retained on the stent by a radial recoil force exerted by the ePTFE tubular graft against the stent.

The covered stent may comprise one or more stents circumferentially retained within a single graft. For example, according to a first preferred embodiment of the invention, a covered stent is made using a single pressure expandable stent circumferentially and longitudinally covered with a single ePTFE tubular graft. In accordance with a second preferred embodiment, the covered stent comprises a pair of balloon expandable stents positioned at opposing ends of a single ePTFE tubular graft with each stent being circumferentially and longitudinally covered by the ePTFE graft, with an intermediate region of the ePTFE tubular graft being unsupported. According to a third preferred embodiment of the invention, a longitudinally articulating covered stent is made by co-axially aligning a plurality of discrete stents in a longitudinally extending array, such that the plurality of stents are in end-to-end relationship with one another, and the entire longitudinal array of stents is circumferentially and longitudinally covered with an ePTFE tubular ePTFE graft.

The present invention is further directed to a method for making the stent-graft assembly and for mounting the stent-graft onto a delivery catheter. In accordance with the method of the present invention, the stent-graft is assembled using a dilation mandrel and a stent mandrel. The inventive method includes the steps of mounting the stent onto the stent mandrel, joining the stent mandrel with the dilation mandrel, positioning the graft onto the dilation mandrel and radially expanding the graft on the dilation mandrel to an inner diameter which is greater than the outer diameter of the stent, passing the radially expanded graft over the stent, trimming excess graft material from the proximal and distal ends of the stent, decoupling the mandrel from the stent mandrel, and removing the covered stent from the stent mandrel. In accordance with the method of mounting the covered stent onto a delivery catheter, the method further includes the steps of disengaging a proximal section of the stent mandrel, engaging a delivery catheter with the stent mandrel such that a balloon section of the delivery catheter is proximate with the covered stent-graft, concentrically positioning the covered stent-graft over the balloon section of the delivery catheter and disengaging the delivery catheter from the stent mandrel.

Radially pressure expandable and self expanding endoluminal stents, such as those disclosed by Palmaz in U.S. Pat. Nos. 4,733,665, 4,739,762 and 5,102,417, Gianturco in U.S. Pat. Nos. 4,580,568 and 4,907,336, Kreamer in U.S. Pat. No. 4,740,207, Wlktor in U.S. Pat. Nos. 4,886,062 and 4,969,458, Pinchuck in U.S. Pat. No. 5,163,958 and Schatz in U.S. Pat. No. 5,195,984 have been clinically investigated over the past several years in an attempt to overcome the limitations of percutaneous transluminal coronary angioplasty (PTCA), particularly restenosis due to fibrocellular intimal proliferation subsequent to PTCA. More recently, investigations have focused on balloon-expandable stents to anchor intraluminal grafts. "Transfemoral Intraluminal Graft Implantation for Abdominal Aortic Aneurysms", *Ann. Vasc. Surg.* 1991, 5: 491–499; "Transluminal Placement of a Prosthetic Graft-Stent Device for Treatment of Subclavian Artery Aneurysm", *J. Vasc. Surg.*, December 1993, 18:1056–1059; and "Percutaneous Femoropopliteal graft Placement", *Radiology*, June 1993, 187:643–648.

Several supported grafts are known in the art. For example, Kubo, et al., U.S. Pat. No. 5,236,447, disclose an artificial tubular organ supported by a supporting frame made of a plastic material, which may be PTFE, and a medical prosthetic material disposed on at least one surface of the supporting frame wherein the prosthetic material is preferably comprised of absorbable and non-absorbable macromolecular yarns which may include PTFE. The medical prosthetic material is joined to the supporting frame by sutures. The sutures attaching the prosthetic material to the supporting frame limit movement of the fabric on the frame. The Kubo, et al. assembly is not radially expandable and is therefore incapable of use in endoluminal applications which require radial expandability.

The Rhodes, U.S. Pat. No. 5,122,154 discloses an endovascular bypass graft comprising a sleeve having a plurality of expandable, ring-like stent members are equidistantly spaced along the longitudinal length and positioned on either the outer or inner surface of the sleeve. The sleeve is formed from a highly flexible material, such as expanded PTFE, and has a series of longitudinally extending pleats. Each stent member is connected to one or more of the longitudinally extending pleats in the sleeve and permit unfolding of the sleeve during radial expansion of the ring-like stent members.

Lee, U.S. Pat. No. 5,123,917, describes a radially expandable supported graft having multiple graft layers. The supported graft includes a flexible cylindrical inner tube having an outer periphery, a plurality of separate scaffold rings mounted on the outer periphery along the longitudinal extent of the inner tube, and a flexible cylindrical outer tube concentrically enclosing the inner tube and scaffold members. The scaffold members are spaced to allow for flexibility of the inner and outer tubes along their longitudinal axis.

Another endovascular graft for repairing aneurysms is described in U.S. Pat. No. 5,211,658 issued to Clouse. The Clouse patent discloses a percutaneously deliverable structural frame and an independently, percutaneously deliverable radially expandable tubular member subsequently placed concentrically within the structural frame. The structural frame preferably comprises a plurality of meshed strands joined to axially spaced end rings wherein both the meshed strands and rings are comprised of a shape memory metal. The tubular member, a thin walled flexible membrane, preferably includes a means for expanding and holding the tubular member against the structural frame. This means may take the form of an outwardly expansible spring coil disposed within the interior of the tubular member.

Kreamer, U.S. Pat. No. 5,078,726, discloses a stent-graft assembly having stents placed inside either one or more ends of a graft. The stents are formed from a rectangular semi-rigid material rolled into an open ended cylinder so that an inside longitudinal edge overlaps an outside longitudinal edge of the material. The stents further comprise a retaining means which acts to restrain the inner longitudinal edge of the graft in the graft's expanded state. In use, the synthetic graft is endoluminally positioned to exclude a weakened section of the vasculature. A stent in its relaxed diameter state is positioned inside the end of a graft and expanded to its enlarged, larger diameter state. The radially expansive force of the stent impinges upon the graft and the inner wall of the blood vessel to prevent displacement of the stent and graft after radial expansion.

Although a number of radially expandable stent-graft delivery systems are particularly suitable for endoluminal delivery and placement are generally known in the art, none of the foregoing radially expandable stent-graft assemblies offers a configuration which inhibits axial displacement of the graft relative to the stent prior to and during endoluminal delivery and radial expansion without the use of adhesives or sutures. Further, none of the previously known stent-graft devices reduces the profile of the stent graft combination thereby enabling the reduced French size of the introducer balloon catheter.

Accordingly, there is a need for a stent-graft assembly which permits use of a reduced size introduction catheter to facilitate easy and safe deployment of the stent-graft assembly within various sizes of blood vessels and at various sites within the blood vessels. There is also a need for a stent-graft assembly which comprises a graft which is retained upon a substantially non-radially expanded stent by inherent radial recoil forces exerted by the graft against the stent during delivery and radial expansion of the stent-graft assembly.

SUMMARY OF THE INVENTION

It is a principal object of the present invention, therefore, to provide an intraluminal stent-graft assembly having a radially expandable stent in a substantially non-radially expanded diameter circumferentially which is covered, about at least a substantial portion of its longitudinal axis, by a tubular graft which is retained about the stent by inherent radial recoil force of the graft upon the stent.

It is a further object of the present invention to utilize a tubular graft made from a microporous longitudinally expanded polytetauoroethylene material and a balloon expandable endoluminal stent.

It is a further object of the present invention to provide a method for assembling the inventive stent-graft which comprises radially dilating a tubular graft made of a material having inherent redial recoil material properties, circumferentially fitting the dilated tubular graft about a radially expandable endoluminal stent, and permitting the dilated tubular graft to recoil to a reduced diameter about the stent. The stent-graft assembly of the present invention is particularly useful in many type of conditions affecting anatomical passageways, such as the repair or exclusion of aneurysms, vascular occlusions either alone or in conjunction with percutaneous transluminal coronary angioplasty (PTCA), occlusions, obstructions or strictures of the biliary ducts, peripheral vasculature, ureters or the urethra.

It is a further object of the present invention to provide an apparatus for assembly of the inventive stent-graft which comprises a stent retaining mandrel having a first diameter and a graft dilation mandrel having a second diameter which is greater than the first diameter of the stent retaining mandrel, which is removably engageable with the stent retaining mandrel.

It is a still further object of the present invention to provide an apparatus for making the expandable stent-graft assembly which comprises interchangeable stent retaining mandrels and graft dilation mandrels for accommodating different radial diameters of tubular grafts and endoluminal stents, and for making different diameter stent-graft assemblies.

It is yet a further object of the present invention to provide a method and apparatus for delivering and positioning an expandable stent-graft within a lumen in the body wherein the stent-graft is assembled and loaded from the manufacturing assembly directly onto a balloon catheter.

Briefly, the expandable stent-graft assembly includes an expandable tubular graft member which circumferentially covers an exterior surface of at least a longitudinal section of a tubular radially expandable stent. The tubular graft member is preferably comprised of sintered, longitudinally expanded polytetrafluoroethylene. More specifically, the radially expandable stent-graft assembly includes a tubular radially expandable stent having an interior or luminal surface and an exterior or abluminal surface and a tubular graft member having an interior or luminal surface and an exterior or abluminal surface, wherein the luminal surface of the tubular graft member contacts the abluminal surface of the radially expandable stent and the tubular graft member is retained about the radially expandable stent, in its substantially unexpanded diameter, by inherent radial recoil forces exerted by the tubular graft member graft upon the radially expandable stent.

The method for maid the expandable stent-graft assembly includes the steps of radially dilating the tubular graft member, concentrically placing the dilated tubular graft member about at least a longitudinal section of a radially expandable stent in its substantially radially unexpanded diameter, removing the dilation force thereby permitting the dilated tubular graft member to diametrically recoil, and permitting the radial recoil properties of the tubular graft member to impinge upon the abluminal surface of the radially expandable stent, thereby concentrically fitting the tubular graft member about the radially expandable stent.

The present invention is also directed toward an apparatus for assembling the inventive radially expandable stent-graft assembly. The apparatus generally includes a) a tapered dilation mandrel comprising a first end having a first diameter and a second end having a second, larger diameter for radially expanding a vascular graft to a larger diameter by sliding the vascular graft from the first end to the second end of the tapered mandrel; b) a stent retaining mandrel having a diameter less than the second, larger diameter of the tapered dilation mandrel; and c) means for releasably connecting the second end of the tapered mandrel to the stent retaining mandrel to permit removal of the resultant stent-graft assembly.

The objects and advantages of the invention will appear more fully from the following more detailed description of the preferred embodiments of the invention made in conjunction with the accompanying drawings.

DETAILED DESCRIPTION OF THE PREFERRED EMBODIMENTS

Figures 1, 2, 3:
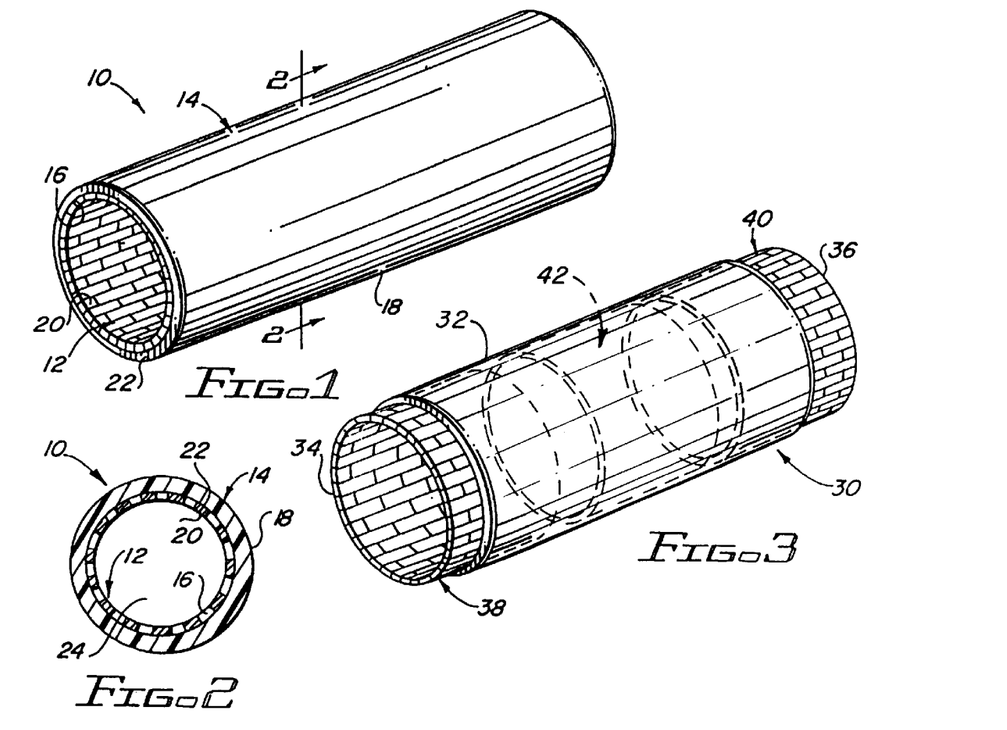
FIG. 1 is a perspective view of the stent cover embodiment of the expandable endovascular stent-graft assembly of the present invention.
FIG. 2 is a cross-sectional view taken along line 2—2 of FIG. 1.
FIG. 3 is a perspective view of the stent-graft embodiment of the expandable endovascular stent-graft assembly of the present invention with the underlying stents located at the ends of the stent-graft shown partially in phantom.

Turning now to the accompanying Figures, the inventive radially expandable endoluminal stent-graft assembly 10 is illustrated generally in FIG. 1. Stent-graft assembly 10 generally consists of a radially expandable stent member 12, in a substantially radially unexpanded diameter, circumferentially covered by a radially expandable tubular graft member 14, which is preferably comprised of longitudinally expanded microporous polytetrafluoroethylene (ePTFE). It will be understood by those skilled in the art that ePTFE materials have a characteristic microstructure consisting of nodes and fibrils, with the fibril orientation being substantially parallel to the axis of longitudinal expansion. Expanded polytetrafluoroethylene materials are made by ram extruding a compressed billet of particulate polytetrafluoroethylene and extrusion lubricant through an extrusion die to form sheet or tubular extrudates. The extrudate is then longitudinally expanded to form the node-fibril microstructure and heated to a temperature at or above the crystalline melt point of polytetrafluoroethylene, i.e., 327° C. for a period of time sufficient to sinter the ePTFE material. The tubular graft member 14 of the present invention is preferably made by ram extruding a PTFE-lubricant billet around a mandrel and through an extrusion die to form a tubular extrudate. The tubular extrudate is longitudinally expanded and sintered, then cut to a desired length as required to circumferentially cover a longitudinal section of the stent member 12.

The tubular graft member 14 comprises an interior or luminal wall surface 16 and an exterior or abluminal wall surface 18. The stent member 12 is also tubular and comprises an interior or luminal surface 20 and an exterior or abluminal surface 22, as illustrated in FIG. 2. When circumferentially disposed about the stent member, the luminal surface 16 of the graft member 14 resides adjacent the abluminal surface 22 of the radially unexpanded stent member 12 to form the expandable stent-graft assembly 10 and retained thereupon by inherent radial recoil properties of the ePTFE tubular graft member 14 acting against the abluminal surface 22 of the stent member which imparts an interference fit between the stent member 12 and the graft member 14. It has been found that all tubular ePTFE graft members exhibit between about 10–30% recoil from the radially expanded diameter, with the median recoil falling between 15–25% of the radially expanded diameter. The radial recoil property of the radially expanded tubular ePTFE material, appears to be a constant property and not dependent upon degree of radial expansion. Moreover, the radial recoil property does not seem affected by other material properties of an ePTFE graft, such as internodal distance, wall thickness, degree of longitudinal expansion, etc.

Once assembled, the radially expandable stent-graft assembly 10 may be placed on a balloon catheter, such as a conventional angioplasty balloon catheter, delivered through an anatomical passageway to a desired delivery site, and placed endoluminally by pressure dilating the balloon thereby radially expanding the stent-graft assembly to a desired diameter based upon preselected expanded diameters of the stent member 12 and the graft member 14.

Radial dilation of the tubular graft member 14, from a pre-expanded diameter which is less than the unexpanded outer diameter of the stent member 12, to a radially expanded inner diameter which is greater than the outer diameter of the stent member 12, imparts a recoil force to the tubular graft member 14. The radial recoil of the radially dilated tubular graft member 14 reduces the inner diameter of the tubular graft member 14 such that the luminal surface 16 of the tubular graft member 14 impinges upon and resides adjacent the abluminal wall surface 22 of the stent member 12, as shown in FIG. 2. In this manner the inventive stent-graft assembly 10 affords a more streamlined endoluminal prosthesis than the currently known implants which require suture attachments between a radially unexpanded stent member and a larger diameter endoluminal graft. Further, because the inventive stent-graft assembly 10 has a reduced profile, the French size of the introducer set for introducing the inventive stent-graft assembly 10, may be correspondingly reduced, further facilitating percutaneous delivery of the expandable stent-graft assembly 10.

Once the stent-graft assembly 10 is delivered endoluminally to a desired position in an anatomical passageway, the inventive stent-graft assembly 10 is radially expanded by application of a radially expansive pressure, such as that provided by an angioplasty balloon, against the luminal wall surface 20 of the stent member 14. Both the stent member 12 and the graft member 14 radially expand to an expanded diameter as desired. During radial expansion, the tubular stent member 12 and the tubular graft member 14 are radially deformed under the influence of a positive pressure exerted against the luminal wall surface 20 of the tubular stent member. The material of the tubular graft member 14 is stretched or expanded with the result that the wall thickness of the radially unexpanded graft member 14 is typically thicker than that of the radially expanded graft member 14 due to radial stretching of the graft member 14. Where the tubular graft member 14 is made of sintered ePTFE, it will be understood, by those in the art, that radial expansion of the ePTFE tubular graft member 14 deforms the node-fibril microstructure of the ePTFE material. Where the ePTFE tubular graft member 14 employed has an axis of longitudinal expansion parallel to the axis of radial expansion of the tubular graft member 14, radial expansion of the stent-graft assembly 10 will result in elongation of the fibrils. Where, however, the ePTFE tubular graft member employed has an axis of longitudinal expansion which is perpendicular to the axis of radial expansion of the tubular graft member 14, radial expansion of the stent-graft assembly 10 results in elongation of the nodes.

The radial recoil force of the tubular graft member 14 against the abluminal wall surface 22 of the stent member aids in preventing axial migration of the graft member 14 on the stent member 12 during radial expansion of the stent-graft assembly 10.

FIG. 3 illustrates second and third embodiments of the inventive radially expandable stent-graft assembly 30. The second embodiment comprises two stent members 38 and 40, a single graft member 32, wherein each of the stent members 38, 40 is positioned at opposing ends 34, 36 of the graft member 32 and retained therein by the radial recoil force of the graft member 32 impinging upon abluminal wall surfaces of the two stent members 38, 40. FIG. 3 illustrates also a third embodiment of the invention which comprises at least three stent members 38, 40 and 42, a single graft member 32, wherein stent members 38 and 40 are positioned at opposing ends 34, 36 of the graft member 32 and stent member 42 is positioned longitudinally between stent members 38 and 40 and each stent member 38, 40 and 42 is retained in the graft member 32 by the radial recoil force of the graft member 32 impinging upon abluminal wall surfaces of the at least three stent members 38, 40 and 42, These embodiments of the inventive stent-graft assembly 30 are particularly well adapted for exclusion of abdominal aortic aneurysms or other trauma to an anatomical passageway, such as by a gunshot, because it has an intermediate longitudinal section of the graft member 32 which is unsupported by any longitudinal section of stent members 38, 40 and 42. Where two or more stent members 38, 40, 42 are used, the intermediate unsupported sections of the graft member 32 permit articulation of the stents 38, 40, 42 relative to each other, with the unsupported sections of graft member 32 acting as articulation joints.

Figure 4:
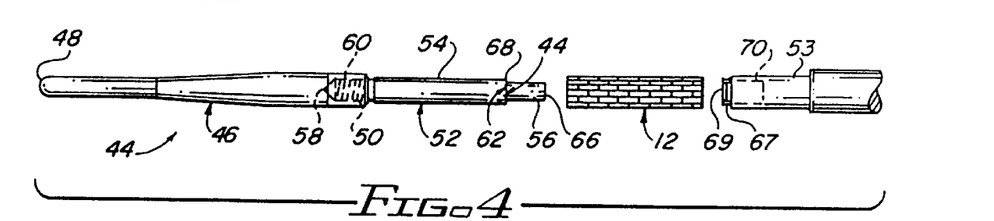
FIG. 4 is a side elevational view of the inventive assembly apparatus for making the expandable endoluminal stent-graft assembly of the present invention showing placement of the unexpanded stent prior to assembling the stent-graft assembly apparatus.

FIGS. 4–17 generally illustrate an assembly apparatus 44 and the method of making the inventive stent-graft assembly 10, as depicted in FIG. 1. FIG. 4 is a partially exploded view of the assembly apparatus 44 used for making the inventive stent-graft assembly. The inventive assembly apparatus 44 comprises generally a tapered dilation mandrel 46 having a first end 48 and a second end 50 wherein the diameter of the second end 50 is greater than the diameter of the first end 48, a stent retaining mandrel 52 which is removably engageable with the second end 50 of the tapered dilation mandrel to retains and supports the stent member 12 in a given position on the stent retaining mandrel and a handle member 53 which is removably coupled to the stent retaining mandrel 52 at one end thereof The stent retaining mandrel 52 has a generally tubular shape and a circular transverse sectional shape. The stent retaining mandrel should have an outside diameter which is less than the inner diameter of the stent member 12 to facilitate loading the stent member onto the stent retaining mandrel, and the combined outside diameter of the stent retaining mandrel 52 and the outside diameter of the stent member 12 is less than the outside diameter of the second end 50 of the tapered dilation mandrel 56.

Figure 5:
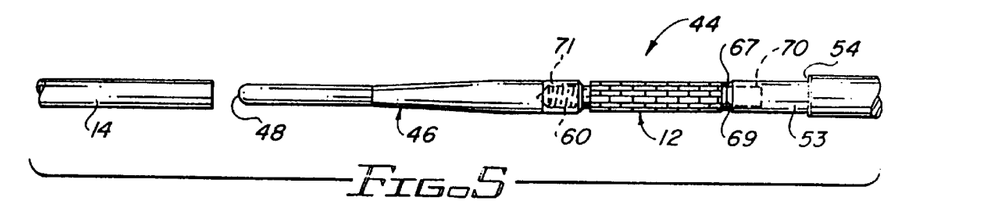
FIG. 5 is a side elevational view, partially shown in longitudinal section, of the assembly apparatus for making the expandable endoluminal stent-graft assembly of the present invention immediately prior to placing the graft onto the mandrel portion of the assembly apparatus.
Figure 6:
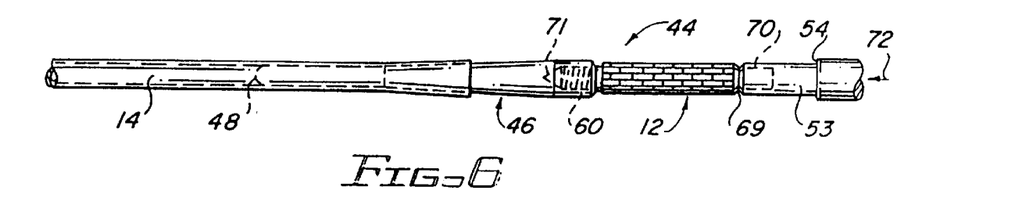
FIG. 6 is a side elevational view, partially shown in longitudinal section, of the assembly apparatus for making the expandable endoluminal stent-graft assembly of the present invention showing the stretching of the graft over the dilation mandrel of the assembly apparatus.
Figure 7:
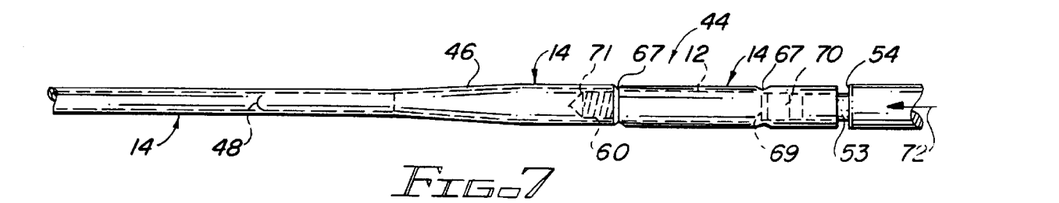
FIG. 7 is a side elevational view, partially shown in longitudinal section, of the assembly apparatus for making the expandable endoluminal stent-graft assembly of the present invention showing sliding of the graft over the larger end of the dilation mandrel and over the unexpanded stent beyond the end of the stent mandrel.

FIGS. 5–7 represent sequential views of the graft member 12 being loaded onto the tapered dilation mandrel 52 and being concentrically engaged about the stent member 12. It can be appreciated that by configuring the outside diameter of the second end 50 of the tapered dilation mandrel to be greater than the outside diameter of the stent member 12 mounted onto the stent retaining mandrel 52, the graft member 14 is radially dilated as it is pulled over the tapered dilation mandrel 46 or as the assembly apparatus 44 is pushed 72 into the lumen of graft member 14. a section of the graft member 14 passes over the stent member 12 mounted on the stent retaining mandrel 52 and is concentrically positioned about the stent member 12. As the graft member 14 is passed over the stent member 12, it encounters no resistance to radial recoil and radially recoils until the luminal surface of the graft member 14 impinges upon the abluminal wall surface of the stent member 12, at which point the graft member 14 continues to exert a positive radial recoil force against the stent member 12, which is resisted radially incompressibility of the stent member 12.

As noted above, the tapered dilation mandrel 46, the stent retaining mandrel 52 and the handle member 53 each have means for removably interconnecting the tapered dilation mandrel 46, the stent retaining mandrel 52 and the handle member 53 to one another along a common longitudinal axis. As illustrated in FIGS. 4–9, the second end 50 of tapered dilation mandrel 52 includes an axially positioned female coupling 58 which receives a mating male coupling 60 on a first end of the stent retaining mandrel 52. While the Figures depict threaded female coupling 58 and male coupling 60, it will be understood by those in the art that the couplings are interchangeable and may be any of a wide variety of suitable couplings, For example, the coupling associated with the tapered dilation mandrel 46 may be a male coupling 60, with a mating female coupling 58 being associated with the stent retaining mandrel 52, or the couplings may be threaded, or non-threaded, such as being an interference fit coupling. The stent retaining mandrel 52 is also removably coupled to the handle member 53 by a male coupling 56 projecting from a second end 62 of the stent retaining mandrel 52. The male coupling 56 removably engages with a female coupling 69 associated with the handle member 53. Again, while the Figures depict a non-threaded coupling between the stent retaining mandrel 52 and the handle member 53, those in the art will understand that the couplings are interchangeable and may be any of a wide variety of suitable couplings, For example, the coupling associated with the stent retaining mandrel 52 may be a female coupling 69, with a mating male coupling 56 being associated with the handle member 53, and the couplings may be threaded, or non-threaded, such as being an interference fit or friction fit coupling.

In accordance with the preferred embodiment of the assembly apparatus 44, the stent retaining mandrel 52 has a generally cylindrical body portion 54 which terminates in shoulder sections 62 at opposing ends of the cylindrical body portion 54 adjacent couplings 50 and 66. When the assembly apparatus 44 is in its fully coupled state, shoulders 62 serve as proximal and distal demarcations for proximal and distal annular detents 67 between the second end 50 of the tapered dilation mandrel 44 and one end of stent member 12 and between the handle member 53 and a second end of stent member 12. The lent of the cylindrical body portion 54 between shoulder sections 62 preferably corresponds to the length of stent member 14. As used in conjunction with the assembly apparatus 44, "distal" refers to a direction corresponding to the relative position of the tapered dilation mandrel 46, while "proximal" refers to a direction corresponding to the relative position of the handle member 53.

FIGS. 4–9 also illustrate the method for making the inventive stent-graft 10 assembly using the assembly apparatus 44. Tapered dilation mandrel 46 is coupled to the stent retaining mandrel 52 by engaging coupling 60 in second end 50 of the tapered dilation mandrel 46 with coupling 60 of the stent retaining mandrel 52. A stent member 12, in its substantially radially unexpanded diameter, is engaged about the stent retaining mandrel 52 by concentrically positioning the stent member 12 about the stent retaining mandrel 52. The handle member 53 is then coupled to the stent retaining mandrel 52 by engaging coupling 56 of the stent retaining mandrel 52 with coupling 69 of the handle member 53. As shown in FIG. 5, the stent member 12 is positioned circumferentially about the stent retaining mandrel 52, and the stent retaining mandrel is positioned intermediate between the tapered dilation mandrel 46 and the handle member 53.

FIG. 6 illustrates the step of engaging the graft member 14 onto the tapered dilation mandrel 44 by applying an axial force 72 to the assembly apparatus 44 which causes the tapered dilation mandrel to pass into and through the lumen of graft member 14. The assemble apparatus 44 is passed into and through the lumen of graft member until the first end of the graft member 14 is in close proximity to a terminal portion 54 of handle member 53. As the graft member 14 passes over the second end 50 of the tapered dilation mandrel 44, the graft member 14 radially expanded so that the inner diameter of graft member 14 is radially expanded to the outer diameter of the second end 50 of the tapered dilation mandrel 44. At the point of the distal annular detent 67, the inner diameter of the graft member 14 is greater than the outside diameter of the stent number 12. As the graft member 14 moved axially over the stent member 12 and to a position adjacent the handle member 53, the graft member 14 undergoes radial recoil so that the inner diameter of the graft member 14 reduces until it meets with resistance to further recoil. As illustrated in FIG. 7, the graft member 12 has radially recoiled onto the stent member 12, and has 818 recoiled into annular detents 67 at the proximal and distal ends of the stent member 12.

Engagement of the graft member 14 over the tapered dilation mandrel 46 is facilitated by forming tabs on the first end of the graft member by cutting longitudinal slits (not shown) along diametrically opposed sides of the graft member. The tabs can then be used to retain the graft member 14 while an axial force 72 is applied to the assembly apparatus, or the tabs may be used to manually pull the graft member 14 over the tapered dilation mandrel 46, the stent member 14 and to the handle member 53. To prevent formation of seams or wrinkles, is important to avoid applying torsional forces to the graft member by twisting the graft during engagement of the graft member onto the assembly apparatus 44.

Figure 8:
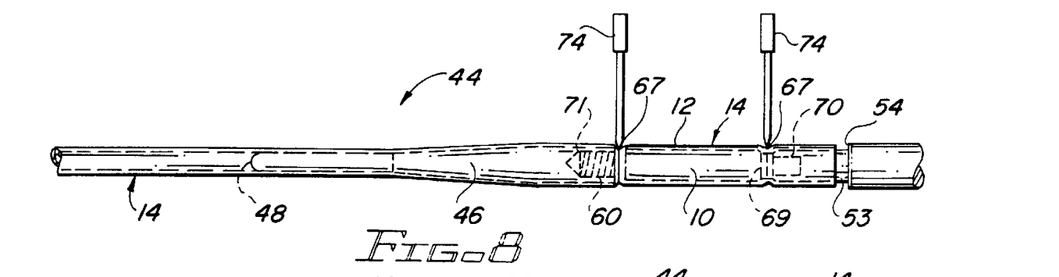
FIG. 8 is a side elevational view, partially shown in longitudinal section, of the assembly apparatus for making the expandable endoluminal stent-graft assembly of the present invention showing circumferential cutting of the graft near the ends of the unexpanded stent.
Figure 9:
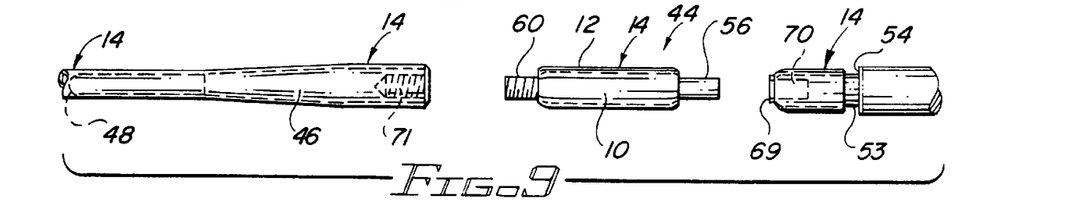
FIG. 9 is a side elevational view, partially shown in longitudinal section, of the assembly apparatus for making the expandable endoluminal stent-graft assembly of the present invention showing disassembly of the assembly apparatus by separating the stent mandrel containing the completed stent-graft assembly from the stent mandrel and the handle member.
Figure 10:
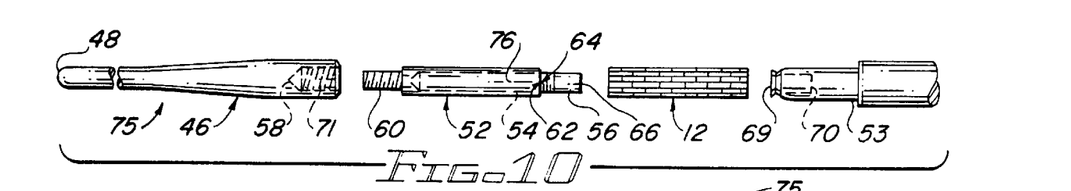
FIG. 10 is a side elevational view of the assembly apparatus for making the expandable endoluminal stent-graft assembly and mounting the stent-graft assembly onto a delivery catheter of the present invention showing placement of the unexpanded stent prior to assembling the assembly apparatus.
Figure 11:
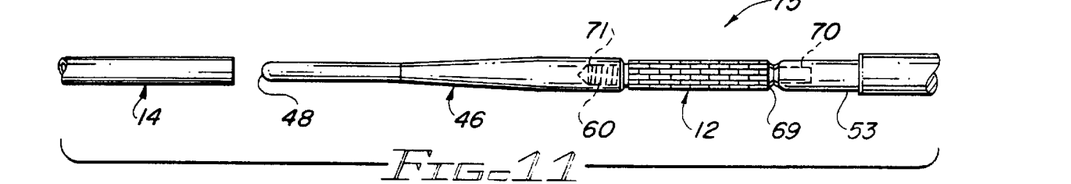
FIG. 11 is a side elevational view, partially shown in longitudinal section, of the assembly apparatus for making the expandable endoluminal stent-graft assembly and mounting it onto a delivery catheter of the present invention immediately prior to placing the graft onto the mandrel portion of the assembled assembly apparatus.
Figure 12:
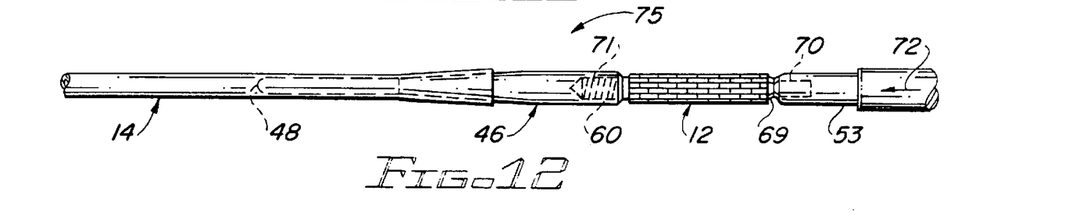
FIG. 12 is a side elevational view, partially shown in longitudinal section, of the assembly apparatus for making the expandable endoluminal stent-graft assembly and mounting it onto a delivery catheter showing the stretching of the graft over the dilation mandrel of the assembled assembly apparatus.
Figure 13:
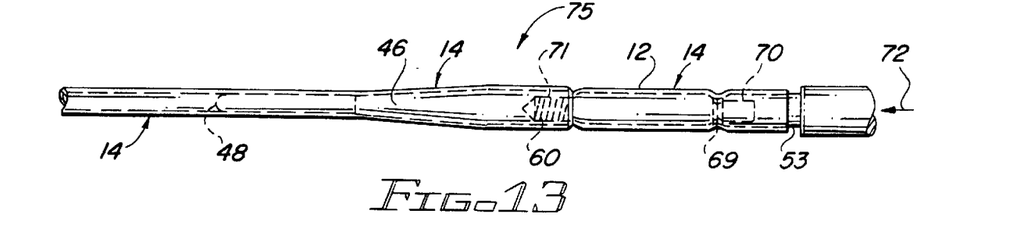
FIG. 13 is a side elevational view, partially shown in longitudinal section, of the assembly apparatus for making the expandable endoluminal stent-graft assembly and mounting it onto a delivery catheter, showing sliding of the graft over the larger end of the mandrel, over the unexpanded stent, and beyond the end of the stent mandrel.
Figure 14:
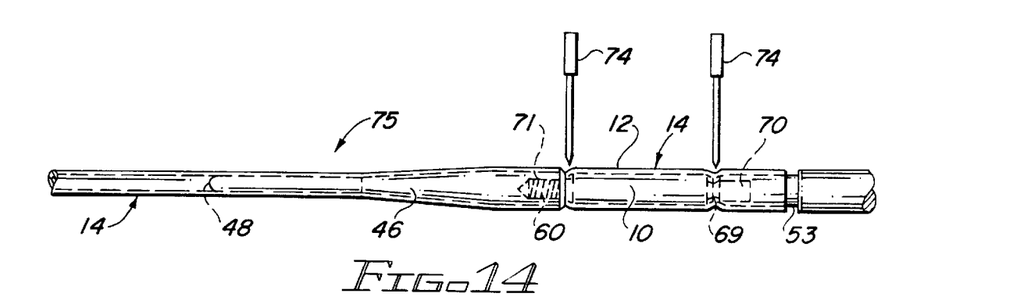
FIG. 14 is a side elevational view, partially shown in longitudinal section, of the assembly apparatus for making the expandable endoluminal stent-graft assembly and mounting it onto a delivery catheter showing the circumferential cutting of the graft near the ends of the unexpanded stent.

FIGS. 8 and 9 illustrate the steps for removing the stent-graft assembly from the assembly apparatus 44. Cutting blades 74 are used make circumferential cuts in the graft member 14 at the position of the annular detents 67, which is slightly, i.e. about 1–2 mm, longer than the longitudinal length of the stent member 12. The remaining section of material of the graft member 14 which projects beyond the opposing ends of stent member 12 allows for the axial foreshortening of the graft 14 in relation to the stent 12 during endoluminal radial expansion of the stent-graft assembly 10.

After making the circumferential cuts at the position of the annular detents 67, the stent-graft assembly 10 is separated from the remainder of the graft member 14. The stent retaining mandrel 52 may be decoupled from the tapered dilation mandrel 46 and the handle member 53 by disengaging the stent retaining mandrel coupling 60 from the tapered dilation mandrel coupling 71 and disengaging the stent retaining coupling 66 from handle member coupling 69 The stent-graft assembly 10 is then removed from the stent retaining mandrel 52 by axially displacing the stent-graft assembly 10 relative to the stent retaining mandrel 52. a waste portion of the graft member 14 resident on the handle member 53 may be discarded. The assembly apparatus 44 is then in condition to reload another unexpanded stent member 12 onto the stent retaining mandrel to reinitiate the inventive method by repeating the above-described steps and produce additional stent-graft assemblies 10.

It will be apparent to those skilled in the art that a multitude of sizes, both in length and in outer diameter, of the stent member 12, the graft member 14 and the assembly apparatus 44 may be employed to make a stent-graft assembly 10 having pre-determined dimensions.

EXAMPLE

A 2.8 mm internal diameter (ID) ePTFE tubular graft was radially stretched over a tapered dilation mandrel having a 3.7 mm external diameter at its largest end. The ePFFE graft was then immediately passed over a 3.4 mm unexpanded stent circumferentially mounted on a stent retaining mandrel which was removably coupled to the tapered dilation mandrel. After being passed over the unexpanded stent, the ePTFE graft exhibited immediate recoil against the outer surface of the stent and assumed a 3.4 mm ID. The graft appeared to be fit tightly about the stent and was resistant to manual displacement along the longitudinal axis of the stent. Subsequent radial expansion of the resultant stent-graft assembly was accomplished by loading the stent-graft assembly onto an angioplasty balloon catheter, applying a positive fluid pressure to the angioplasty balloon to radially expand the stent-graft assembly to 10 mm OD. At its expanded diameter, the graft remained tightly fit about the circumference of the stent and exhibited resistance to axial displacement upon manual manipulation.

FIGS. 10–17 depict the inventive method and assembly apparatus 75 for making and mounting the expandable endoluminal stent-graft assembly onto a delivery catheter. More specifically, FIGS. 10–14 are replicates of FIGS. 4–8 with the exception that the stent retaining mandrel 52 includes a central closed-end longitudinal bore 76, in FIG. 15, which opens toward the proximal end of the assembly apparatus 75 adjacent the handle member 53.

Figure 15:
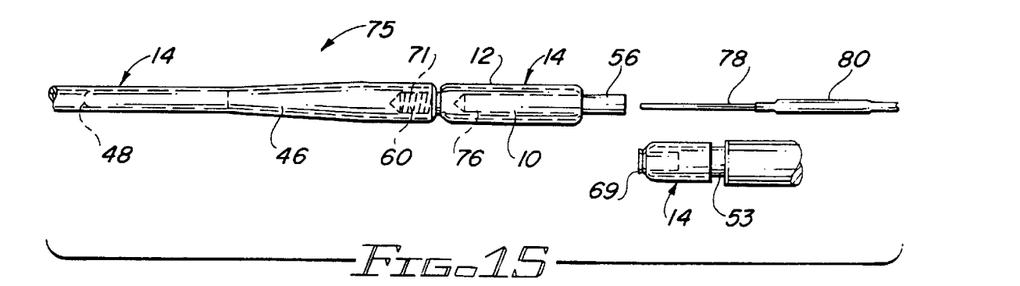
FIG. 15 is a side elevational view, partially shown in longitudinal section, of the assembly apparatus for making the expandable endoluminal stent-graft assembly and mounting it onto a delivery catheter showing removal of the handle member bar from the stent mandrel and the positioning the balloon catheter relative to the stent mandrel.
Figure 16:
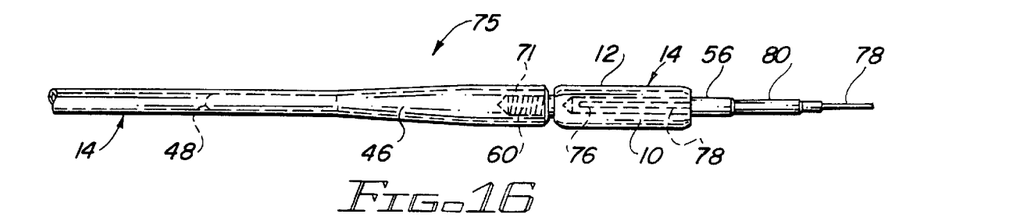
FIG. 16 is a side elevational view, partially shown in longitudinal section, of the assembly apparatus for making the expandable endoluminal stent-graft assembly and mounting it onto a deliver catheter of the present invention showing the insertion of the balloon catheter into the lumen of the stent mandrel.
Figure 17:
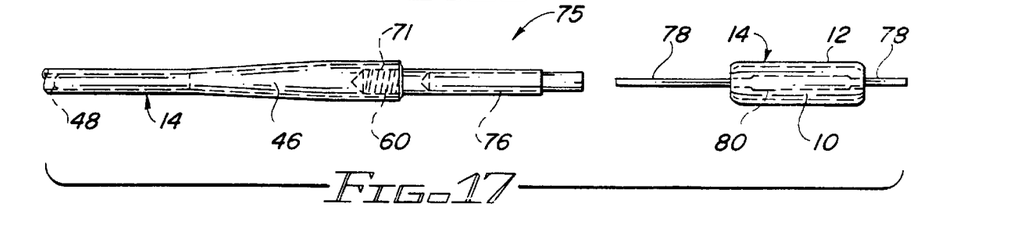
FIG. 17 is a side elevational view, partially shown in longitudinal section, of the assembly apparatus for making the expandable endoluminal stent-graft assembly and mounting it onto a delivery catheter of the present invention showing removal of the expandable endoluminal stent-graft assembly mounted onto a delivery catheter from the stent mandrel after positioning the stent-graft cover over the center of the balloon on the balloon catheter.

The procedure for make the stent-graft assembly 10 follows the same steps in FIGS. 10–14 described above with reference to FIGS. 4–8. However, as illustrated in FIG. 15, after the circumferential cuts in the graft member 14 are made at the position of the annular detents 67, the handle member 53 is disengaged from the stent retaining mandrel 52. a distal tip of a balloon catheter, having an inflatable balloon 80, is then passed into the longitudinal bore 76 such that the balloon 80 is positioned in proximity to the stent-graft assembly 10 as illustrated in FIG. 16. The stent-graft assembly 10 is then displaced from the stent retaining mandrel 52 and concentrically positioned about the inflatable balloon 80 of the balloon catheter 78. Finally, as shown in FIG. 17, the balloon catheter 78 is removed from the longitudinal bore 76 in the stent retaining mandrel 52, thereby providing an pre-mounted stent-graft delivery system.

The resulting radially expandable endoluminal stent-graft assembly has an added advantage of lowering the expansion pressure required to radially expand the stent-graft assembly due to the pre-expansion of the ePTFE graft during the inventive process.

In accordance with the preferred embodiments of the present invention, it is preferred that a PALMAZ stent (Johnson & Johnson Interventional Systems, Inc., Warren, N.J.), as described by Palmaz in U.S. Pat. No. 4,733,665, or balloon expandable PALMAZ-type stents be used. However, other different types of pressure expandable stents known in the art may be used, with the only limitation being that the exhibit sufficient radial strength to resist the radial recoil of a radially expanded ePTFE tubular graft. It is also preferable that the assembly apparatus 44 be made of a material which is resistant to burr formation, such as stainless steel, and which provides smooth surfaces which do not damage the graft member while it is being manipulated on the assembly apparatus. The inventive process may be carried out at room temperature, or may be carried out at elevated temperatures which are below the crystalline melt point of PTFE. In this manner, there is provided a covered stent in which the cover is retained by an interference fit between the cover and the stent and no adhesives or sutures are required to positionally affix the cover onto the stent.

While preferred embodiments of the invention have been shown and described, it will be apparent to those skilled in the art that various modifications may be made in these embodiments without departing from the spirit of the present invention. Therefore, all suitable modifications and equivalents fill within the scope of the invention.

We claim:

1. A radially expandable stent-graft assembly, comprising:
   a tubular radially expandable stent; and
   a tubular graft member having radial recoil properties, wherein said graft member is circumferentially disposed about at least a portion of a longitudinal length of said stent, is radially expandable with said stent, and is retained thereupon by inherent recoil pressure in the range of about 10% to about 30%, exerted by the tubular graft member about the tubular radially expandable stent.

2. The expandable stent-graft assembly of claim 1, wherein said expandable tubular graft member further comprises an expanded polytetrafluoroethylene material.

3. The expandable stent-graft assembly of claim 1, wherein said expandable tubular graft circumferentially covers an entire longitudinal section of the tubular radially expandable stent.

4. The expandable stent-graft assembly of claim 1, wherein said tubular radially expandable stent and said expandable vascular graft are substantially equal in length.

5. A radially expandable covered stent, comprising:
   a tubular radially expandable stent having luminal and abluminal wall surfaces; and
   a tubular graft member having luminal and abluminal wall surfaces and having elastic recoil properties, wherein the luminal wall surface of the graft member circumferentially covers at least a substantial longitudinal aspect of the tubular radially expandable stent and the radial recoil properties of the graft member enable the luminal wall surface of the graft member to exert pressure on the abluminal wall surface of the stent wherein the graft member is adapted to be retained on at least a substantial longitudinal aspect of the tubular radially expandable stent without further retaining means used therewith.

6. The expandable stent cover of claim 5, wherein said graft member further comprises an expanded polytetrafluoroethylene material.

7. The expandable stent cover of claim 5, wherein said graft member circumferentially at least substantially covers the abluminal wall surface of the stent.

8. The expandable stent cover of claim 5, wherein said tubular shaped expandable stent and said expandable vascular graft are equal in length upon final radial expansion of the stent cover.

9. An expandable endovascular stent-graft, comprising:
   a plurality of radially expandable endovascular stents, each having an interior and an exterior surface, wherein each of said stents is conformed to maintain an expanded diameter upon dilation without the use of retaining means; and
   a radially expandable endovascular graft having a first end, a second end, an interior surface and an exterior surface wherein the interior surface of the vascular graft is friction fit about at least a portion of the exterior surface of each of said expandable stents.

10. The expandable endovascular stent-graft of claim 9, wherein the plurality of endovascular stent members further comprises first and second stents which are positioned and retained within the first and second ends of the radially expandable endovascular graft, respectively.

11. The expandable endovascular stent-graft of claim 10, further comprising at least three endovascular stent members, wherein a third stent member is entirely covered by and retained within the radially expandable endovascular graft and positioned intermediate between the first and second stents along the longitudinal axis of the radially expandable endovascular graft.

12. The expandable endovascular stent-graft of claim 9, wherein said radially expandable endovascular graft is comprised of expanded polytetrafluoroethylene.

13. The expandable endovascular stent-graft of claim 9, wherein the expandable vascular graft covers at least a substantial longitudinal extent of each of said plurality of radially expandable endovascular stents.

14. An expandable endovascular stent-graft, comprising:

at least three radially expandable endovascular stent members, each having an interior and an exterior surface wherein a first radially expandable endovascular stent member and a second radially expandable endovascular stent member are positioned and retained within a first end and a second end of a radially expandable endovascular graft and a at least a third radially expandable endovascular stent member is entirely covered by and retained within the radially expandable endovascular graft and positioned intermediate between the first and second stent members along a longitudinal axis of the radially expandable endovascular graft; and the radially expandable endovascular graft further comprising an interior surface and an exterior surface wherein the interior surface of the radially expandable endovascular graft is friction fit about at least a portion of the exterior surface of each of said radially expandable stent members prior to any expansion of the expandable stent-graft.

15. The expandable stent-graft assembly of claim 1, wherein said graft member further comprises an expanded polytetrafluoroethylene material.

* * * * *